United States Patent [19]

Lübbers et al.

[11] Patent Number: 5,057,431

[45] Date of Patent: Oct. 15, 1991

[54] DEVICE FOR OPTICAL MEASURING OF PHYSICAL DIMENSIONS AND MATERIAL CONCENTRATIONS

[75] Inventors: Dietrich W. Lübbers, Dortmund; Klaus P. Völkl, Lüdinghausen; Norbert Opitz, Schwerte, all of Fed. Rep. of Germany

[73] Assignee: Max Planck Gesellschaft Zur Förderung Der Wissenschaften, Göttingen, Fed. Rep. of Germany

[21] Appl. No.: 245,342

[22] Filed: Sep. 15, 1988

Related U.S. Application Data

[63] Continuation-in-part of Ser. No. 882,639, Jul. 7, 1986, abandoned, which is a continuation of Ser. No. 557,191, Dec. 1, 1983, abandoned, which is a continuation of Ser. No. 222,514, Jan. 2, 1981, abandoned.

[30] Foreign Application Priority Data

Jan. 18, 1980 [DE] Fed. Rep. of Germany ....... 3001669

[51] Int. Cl.$^5$ .............................................. C12M 1/40
[52] U.S. Cl. ..................................... 435/288; 435/291; 435/817; 356/436; 356/441; 422/82.06; 422/82.07; 422/56; 422/57; 422/58; 422/73; 436/533; 436/169; 436/172; 436/178
[58] Field of Search ............... 422/58, 82.06, 82.07, 422/50, 52, 55, 56, 57, 68.1, 86, 91, 73; 436/532, 533, 166, 169, 170, 172, 178; 356/39, 246, 436, 441; 435/181, 805, 299, 288, 291, 817; 350/96.29

[56] References Cited

U.S. PATENT DOCUMENTS

| | | |
|---|---|---|
| Re. 31,879 | 5/1985 | Lubbers et al. .................... 422/86 |
| 3,404,962 | 10/1968 | Medlar et al. ..................... 23/253 |
| 3,616,251 | 10/1971 | Linoli ................................. 195/99 |
| 3,684,451 | 8/1972 | Linoli et al. ...................... 23/230 R |
| 3,754,867 | 8/1973 | Guenther .......................... 23/254 R |
| 3,836,433 | 9/1974 | Wirth et al. ....................... 195/68 |
| 3,904,373 | 9/1975 | Harper .............................. 424/7 |
| 4,001,583 | 1/1977 | Barrett .............................. 250/303 |
| 4,003,707 | 1/1977 | Lubbers et al. .................. 23/232 R |
| 4,200,110 | 4/1980 | Peterson et al. .................. 128/634 |
| 4,215,940 | 8/1980 | Lubbers et al. ................... 356/41 |
| 4,255,053 | 3/1981 | Lubbers et al. ................... 422/83 |
| 4,269,516 | 5/1981 | Lubbers et al. ................... 356/39 |
| 4,272,484 | 6/1981 | Lubbers ............................ 422/68 |
| 4,272,485 | 6/1981 | Lubbers ............................ 422/68 |
| 4,306,877 | 12/1981 | Lubbers ............................ 422/82.07 |
| 4,344,438 | 8/1982 | Schultz ............................. 128/634 |
| 4,399,099 | 8/1983 | Buckles ............................. 422/58 |
| 4,516,022 | 5/1985 | Lindgren .......................... 250/227 |
| 4,548,907 | 10/1985 | Seitz et al. ........................ 422/82.07 |
| 4,557,900 | 12/1985 | Heitzmann ....................... 422/87 |
| 4,560,248 | 12/1985 | Cramp et al. .................... 350/96.34 |
| 4,568,518 | 2/1986 | Wolfbeis et al. .................. 422/56 |
| 4,587,101 | 5/1986 | Marsmer et al. ................. 422/56 |
| 4,666,672 | 5/1987 | Miller et al. ...................... 422/82.07 |
| 4,682,895 | 7/1987 | Costello ............................ 350/96.29 |
| 4,762,799 | 8/1988 | Seitz et al. ........................ 422/82.07 |
| 4,857,273 | 8/1989 | Stewart ............................. 350/96.34 |
| 4,861,727 | 8/1989 | Havenstein et al. ............. 252/301.36 |
| 4,877,747 | 10/1989 | Stewart ............................. 350/96.34 |
| 4,900,933 | 2/1990 | Nestor et al. .................... 250/252.1 A |
| 4,925,268 | 5/1990 | Iyer et al. ......................... 350/96.34 |
| 4,943,364 | 7/1990 | Koch et al. ....................... 204/415 |

OTHER PUBLICATIONS

Gehrich et al., Optical Fluorescence and Its Application to an Intra-Vascular Blood Monitoring System, IEEE on Biomed. Eng. vol. 33, No. 2, 2/86, pp. 117-132.

Primary Examiner—Richard V. Fisher
Assistant Examiner—John J. Bruckner
Attorney, Agent, or Firm—Michael J. Striker

[57] ABSTRACT

An optode designed to prevent washing away of the indicator and reagent from a membrane is located within an optical device that measures substance concentrations. The reagent and indicator materials are covalently bound on the membrane. The membrane can be a polysaccharide, especially cellulose, an acid glycol ester, or it can contain silicon. The indicator and/or reagent can be covalently bound to the membrane by a bridge molecular, particularly a multifunctional aldehyde, glutaraldehyde or a silane.

17 Claims, 4 Drawing Sheets

DEVICE FOR OPTICAL MEASURING OF PHYSICAL DIMENSIONS AND MATERIAL CONCENTRATIONS

CROSS-REFERENCE TO RELATES APPLICATIONS

This application is a continuation-in-part of patent application Ser. No. 882,639, filed on July 7, 1986, which in turn is a continuation of patent application Ser. No. 557,191 filed on Dec. 1, 1983, which in turn is a continuation of patent application Ser. No. 222,514 filed on Jan. 2, 1981 all now abandoned.

BACKGROUND OF THE INVENTION

The invention relates to a device which performs optical measurements of particle concentrations. More particularly, it relates to such a device which comprises a light measuring device encompassing a radiation source, monochromator, light receiver and indication device, and also includes a chamber which is measurable by the light measuring device. The chamber may be closed by a membrane and contains at least one indicator material.

In devices of the aforementioned type, the reaction materials or reagent and indicator materials have been sealed into membranes. When measuring particle concentrations, this sealing must be overcome by these particles by permeation. Thus, the quantity of the particles which is available for measuring is permeation dependent, resulting in the measuring process being subject to considerable time constants. On the other hand, if the membranes were made more permeable for the particles to be measured, a washing out of the reaction or indicator materials from the chamber would begin.

SUMMARY OF THE INVENTION

It is therefore an object of the invention to prevent the washing out of the indicator and reagent while simultaneously reducing the permeation resistance of the sheath membrane.

This object is achieved by providing an optical device in which both the reagent and the indicator material are covalently bound to the membrane.

The advantage obtained by use of such device is that the retention of the indicator material and reagent to the membrane is not effected by changes in its permeability. For example, by etching a membrane, the membrane may be made permeable for large molecules without releasing the indicator provided on the membrane for optical measuring. Thereby, rapidly reacting indicator foils may be made, wherein the "optodes," such as measuring elements are called, react to the particle concentrations by color change. They replace the hitherto used devices consisting of a membrane sheath and an indicator enclosed therein, by a single membrane with covalently bound reagent and the indicator.

In addition to the indicator chambers, which are also referred to as "optodes," reaction chambers with reagent are used which are optically controlled or measured, to change the particles being measured in a targeted manner. For example, a reagent may be used in order to replace a particle type which is present in the measuring chamber by a better measurable particle type or intermediate species, as is possible when, e.g., measuring glucose. In a reaction chamber, an enzyme is arranged which reacts with glucose to make oxygen, and thereby consumed oxygen is determinable by the use of optodes. The reaction chamber serves to replace glucose with another particle type, since glucose cannot be optically directly detected. Thus oxygen is very well measurable in an optical-flourescence manner in optodes which, for example contain pyrene butyric acid as an indicator. However, this replacement has limited diffusion because the enzyme and the additional substances required for a reaction must be enclosed in a membrane sheath.

The advantage of this device is the simultaneous rigid anchoring and the easy accessibility of the reaction substances for the particles to be measured, e.g., the covalent binding of indicators on membranes.

The covalent binding of indicators or reagents, or both on a membrane, results in having the adjustment of the devices of the particles to be measured, improved due to the separation of the means for fixing the active substances in the device from the mechanical characteristics of the membrane. For example, this includes the porosity of the membrane, so that the specificity of the total devices for the particles to be measured or to be influenced is also to be increased, while at the same time, a homogenization or the reactive active surfaces is also obtainable. This is because not only the geometric, but also the stoichiometric conditions are maintained during the bonding of the active materials onto the membrane. As a result, the calibration as well as the handling of the devices is considerably improved. Additionally, the durability is improved, in particular, due to the effectiveness of the used indicators and reagents which are solvent independent.

Furthermore simple adjacent chambers (reagent space and indicator space) may now be used, because an indicator is bound on one side of the membrane and a covalently bound reagent is on the other side. Thereby, the replacement of one particle type by another and the simultaneous measuring with the indicator can be performed at a very low time constant, because at the same time a large face presence of reagent for the substance to be replaced and indicator for the replaced substances are available without loss of reagent or indicator material due to washing out, as is the case with currently known devices.

It is particularly advantageous to make the membrane by polymerization. In this case it is possible to initiate the chemical reaction which results in the covalent binding during the manufacture of the membrane so that a homogeneous membrane is obtained, containing the active material.

Particularly suitable materials are polysaccharides, due to the present reactive OH-groups, whereby, in particular, the cellulose offers the opportunity to form foils of a smaller thickness. Methods are known for this purpose with which the permeability is able to be influenced through permeation of particles for wide ranges of particle sizes. The membrane can be of a cellulose derivative.

Another type of advantage is offered by membranes which contain silicon or silicon derivatives. In this case, by silanization of the surface, the possibility is created to covalently bind substances through bridge molecules which otherwise would not react with the membranes. Silicon rubber is such a substance which can be processed into membranes which, in addition, is highly gas permeable. If water vapor permeability is required, one can use acid glycol ester, such as polyterephtal acid glycol ester foil.

As a means for silanization, a 3-(triethoxysilyl)propyl amine is particularly suitable. Multifunctional aldehyde is very suitable as bridge substances, for example, glutaraldehyde.

In particular, when rapid reacting reaction optodes are required, a further advantage is obtainable in that the indicator substances and the reagents are bound covalently to a membrane.

When using bridge substances, it is not only possible to covalently immobilize indicators and/or reagents on a membrane, but also to immobilize indicators which are enclosed in microoptodes so that the sheath of the microoptodes are chemically bound with the membrane, e.g., by means of a silane. Thereby, a further broadening of the substance groups is obtained with which particle concentrations or physical parameters may be optically determinable.

If need be, the membrane together with the covalently bound active substances, reagents and indicators may be made optically effective by known means, for example, blackening, metallizing, or causing diffusion, so that the optical measuring is facilitated in an individual case.

It is also possible that both the microoptodes, and a reagent or indicator are covalently bound to the membrane.

DESCRIPTION OF THE PREFERRED EMBODIMENTS

In the following, some examples for devices in accordance with the present invention are given. The first example concerns the combination of an oxygen indicator covalently with a polysaccaride.

An example for such a system is the substance combination cellulose-pyrene butyric acid which results in a thin indicator mounted optode foil:

The binding of the indicator on the cellulose may only occur at locations of the indicator molecules which do not have any substantial influence on the fluoresence characteristic of the molecule through which the measurement of oxygen is carried out. Since the influence of the carboxyl group on the fluorescence is lower, an esterification of the pyrene butyric acid on the cellophane foil is provided. For this purpose, the pyrene butyric acid with thionyl chloride is converted into pyrene butyric acid chloride:

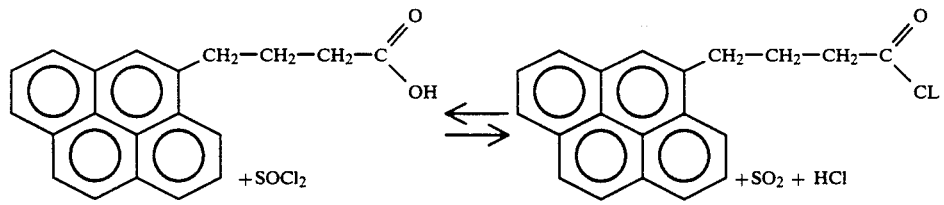

Thereafter, the pyrene butyric acid is released from superfluous thionyl chloride, dissolved in pyridine and with cellophane foil

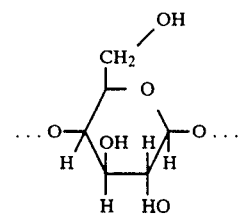

esterified:

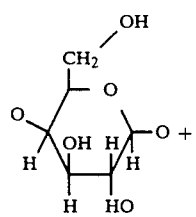

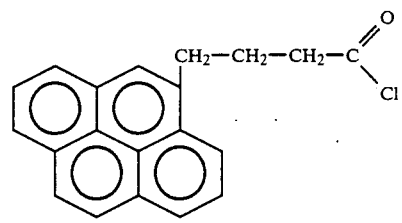

Thereby, pyrene, butyric acid cellulose ester is obtained:

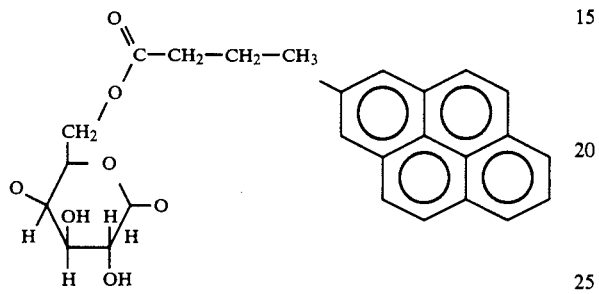

No changes of the fluorescence characteristics occur with respect to the pyrene butyric acid. The reaction time of the indicator bound on a 12 μ cellophane foil is between 2–3 seconds.

The covalent binding of indicators I, as well as reagents, for example, enzyme E, can occur using cyanogen bromide, when the indicators or the reagents have free amino groups (like the -amino groups at lysine or the ε-amino group at N-terminal amino acids), according to the following reaction:

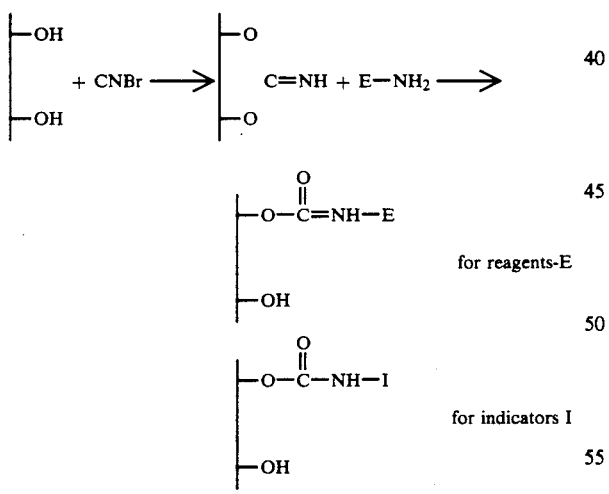

A further method for covalent binding of reagents or indicator substances is the silanization of surfaces, for example, by 3-(triethoxysilyle)-propyl amine. Thereby, an amino group is created on which the reagents or indicators may be bound with a silicon rubber membrane, M, in accordance with the following reaction scheme:

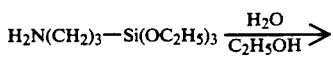

-continued

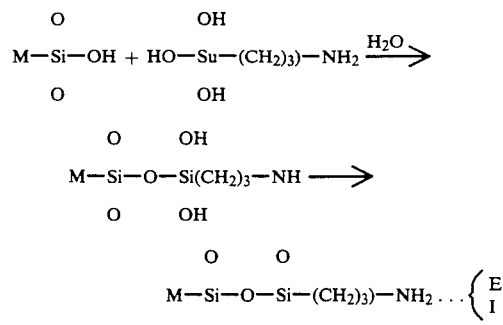

In accordance with known methods, indicators, I, as well as enzyme E, may be bound on the amine group of the activated membrane surface. For example, through cyanur chloride:

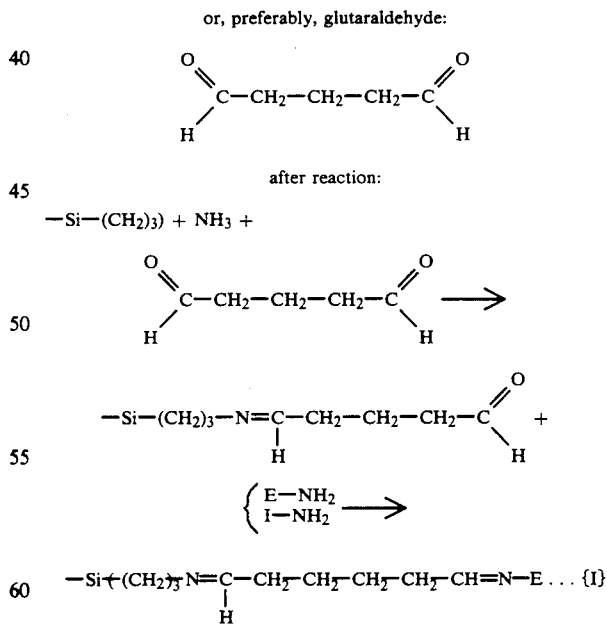

Figure 1:
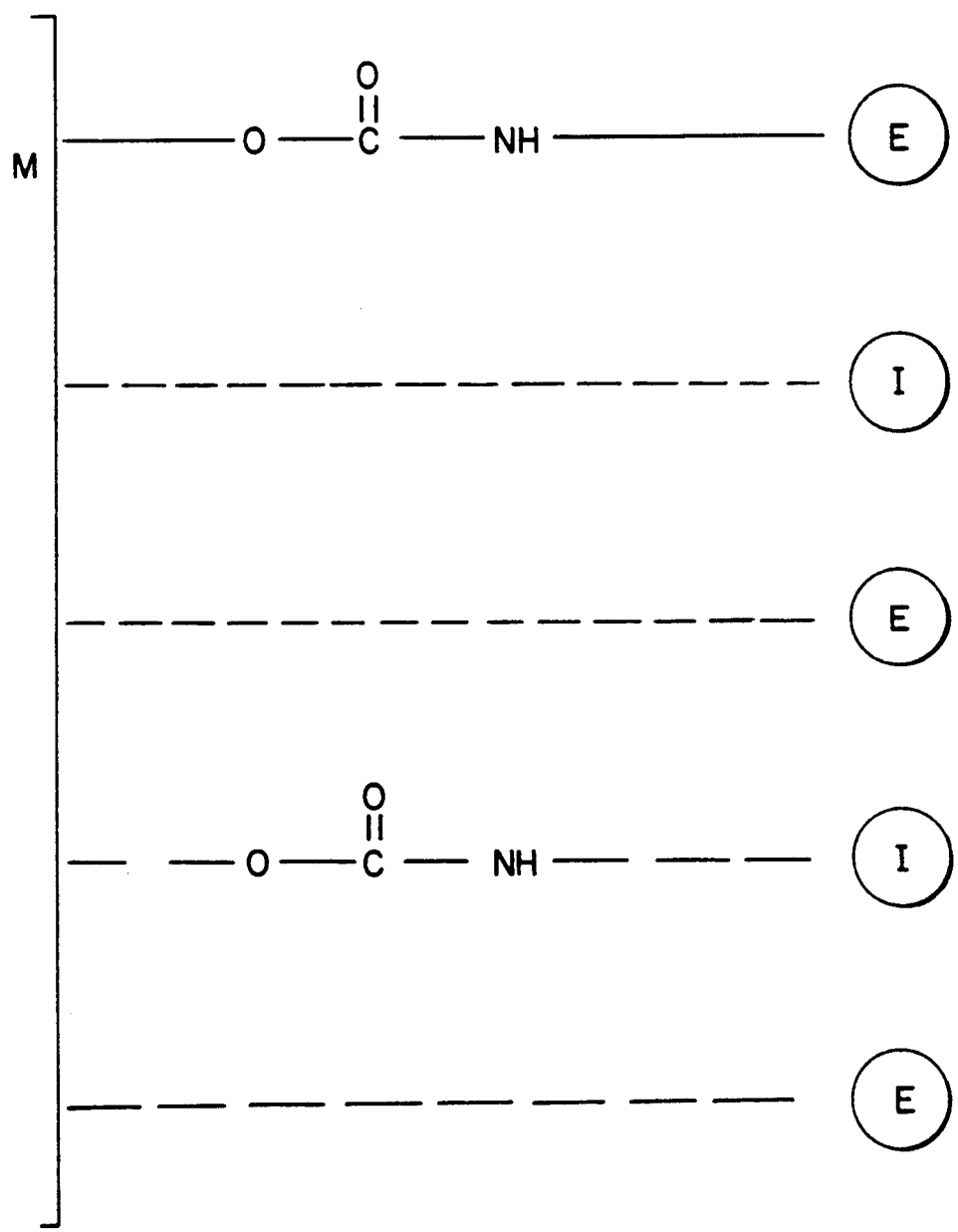
FIG. 1 shows a section of an optode with indicators I and reagents (enzymes) bound covalently to membrane M.
Figure 2:
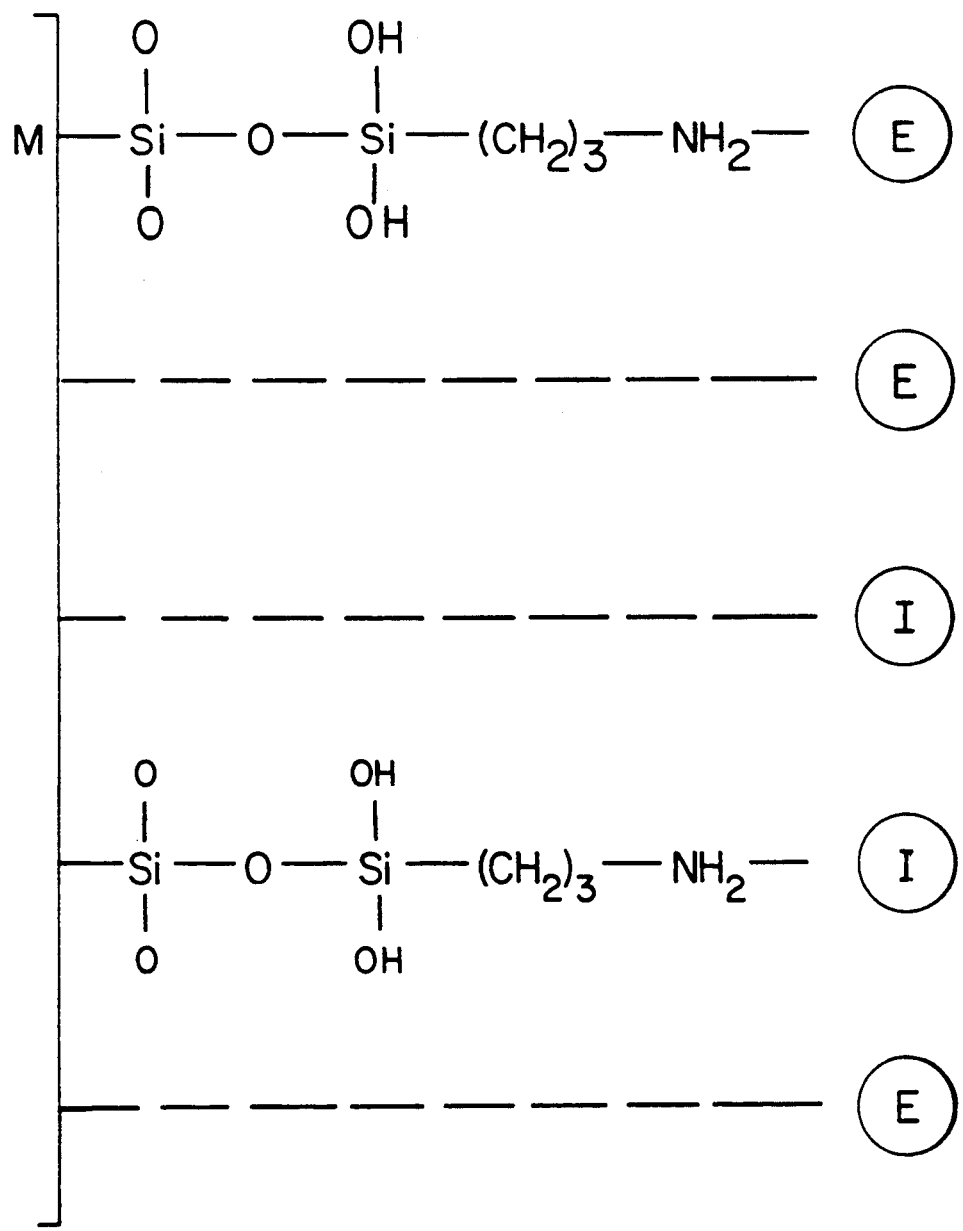
FIG. 2 shows silanization of the membrane surface to create amino groups on which reagent or indicator materials may be bound.
Figure 3:
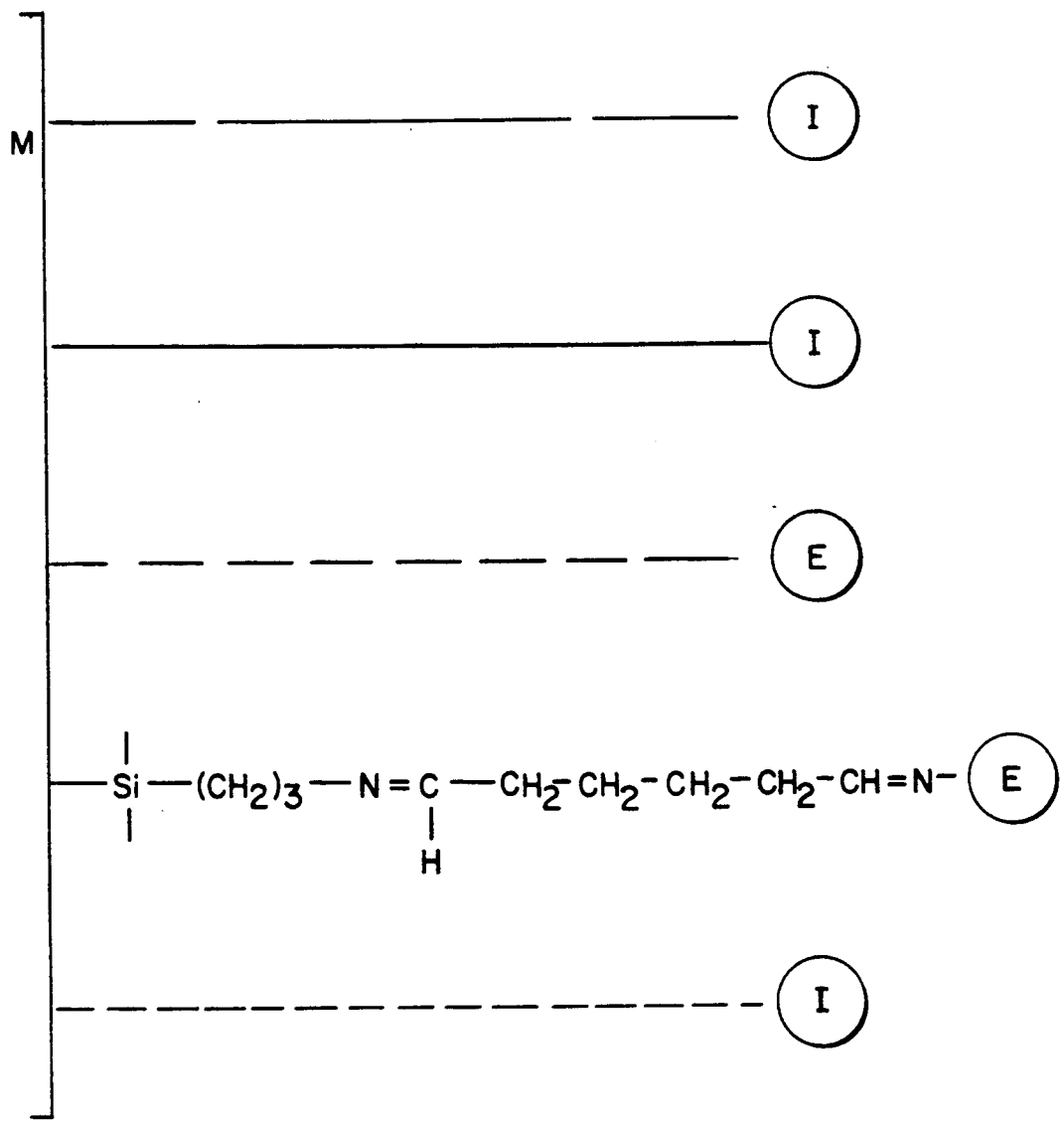
FIG. 3 shows the use of molecular bridges between the membrane and substances to be immobilized.
Figure 4:
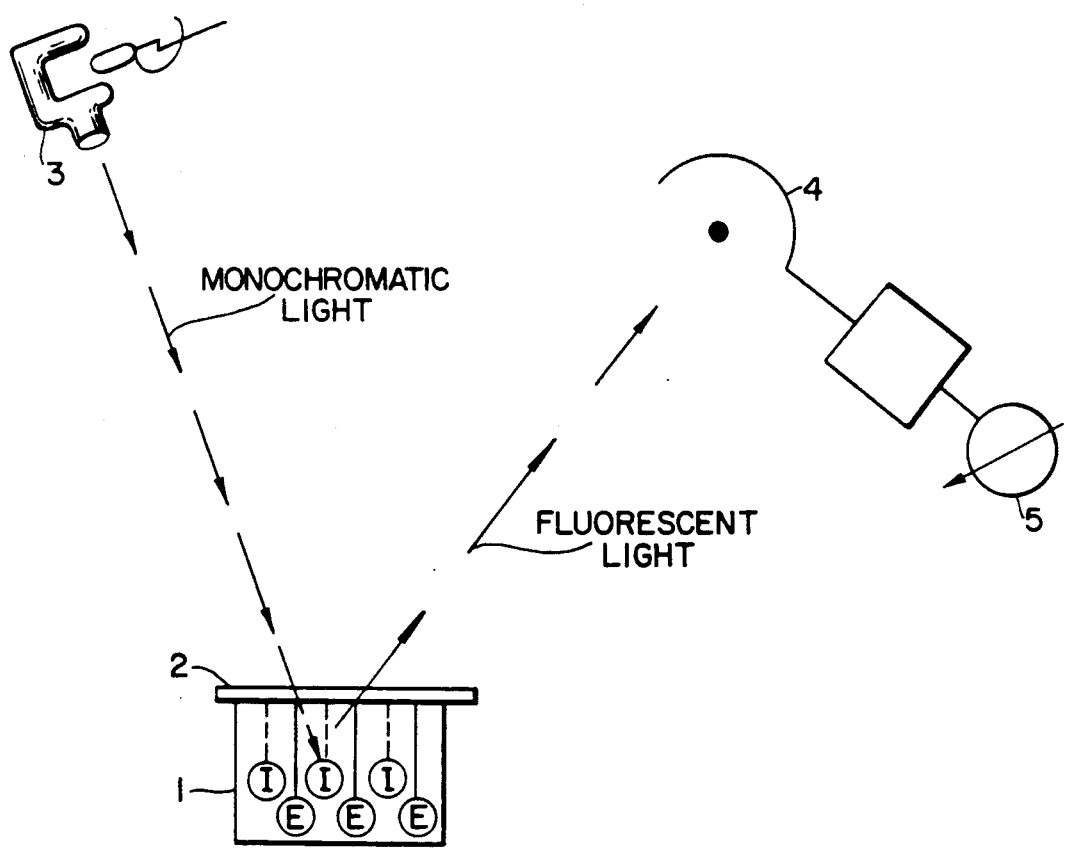

This compound is very protective so that enzymes can be covalently immobilized. The compound is also an example for the use of molecular bridges between the carrier substance (membrane) and the substances to be immobilized. The membrane with the indicator, I, and reagent, E, bound as shown in FIGS. 1 to 3, forms a portion or section of the optode in the device for optical measurement of a particle concentration according to the invention. The remaining portion of the device contains components which are known. The indicator is generally located in and/or defines an indicator space or chamber, while the reagent generally is located in and/or defines a reagent space or chamber.

The particles to be measured are reacting with the bonded enzymes E and the reaction product is changing the fluorescence of the indicator I.

While only several embodiments and examples of the present invention have been shown and described, it is obvious that many changes and modifications may be made thereunto, without departing from the spirit and scope of the invention.

We claim:

1. A device for optical measurement of a particle concentration comprising:
    means for introducing particles;
    a membrane;
    at least one indicator material defining an indicator space, said indicator material emitting light upon light-excitation; and
    a reagent which reacts with said particles to form an intermediate species, said intermediate species effecting said emitting of light from the indicator material, said reagent defining a reagent space;
    wherein said at least one indicator material and said reagent are both covalently bound to said membrane.

2. Device in accordance with claim 1, wherein said reagent comprises a plurality of reagent molecules and said indicator material comprises a plurality of indicator molecules; and wherein the covalent binding of the indicator material and the reagent to the membrane occurs via bridge molecules, each of said reagent molecules being attached to said membrane by one of said bridge molecules and each of said indicator molecules being attached to said membrane by one of said bridge molecules.

3. Device in accordance with claim 2, wherein said bridge molecules are silanes.

4. Device in accordance with claim 2, wherein said bridge molecules are multifunctional aldehydes.

5. Device in accordance with claim 4, wherein said bridge molecules are glutaraldehydes.

6. Device in accordance with claim 1, wherein said membrane comprises a polymer.

7. Device in accordance with claim 6, wherein said polymer consists of a polysaccharide.

8. Device in accordance with claim 7, wherein said polysaccharide is selected from the group consisting of cellulose and cellulose derivatives.

9. Device in accordance with claim 6, wherein said polymer consists of acid glycol esters.

10. Device in accordance with claim 1, wherein said membrane contains a material selected from the group consisting of silicon and silicon derivatives.

11. Device in accordance with claim 10, wherein said membrane consists of silicone rubber.

12. Device in accordance with claim 1, wherein said indicator material and said reagent are enclosed in microoptodes.

13. Device in accordance with claim 12, wherein said microoptodes are covalently bound to said membrane.

14. Device in accordance with claim 1, wherein said membrane is blackened.

15. Device in accordance with claim 1, wherein said membrane is metallized.

16. Device in accordance with claim 1, wherein said reagent is an enzyme which produces oxygen from said particles.

17. Device in accordance with claim 1, wherein said indicator comprises pyrene butyric acid.

* * * * *